(12) United States Patent
Datskos et al.

(10) Patent No.: US 8,505,382 B2
(45) Date of Patent: Aug. 13, 2013

(54) NONLINEAR NANOMECHANICAL OSCILLATORS FOR ULTRASENSITIVE INERTIAL DETECTION

(75) Inventors: Panagiotis George Datskos, Knoxville, TN (US); Nickolay V. Lavrik, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 426 days.

(21) Appl. No.: 13/024,797

(22) Filed: Feb. 10, 2011

(65) Prior Publication Data

US 2012/0206594 A1    Aug. 16, 2012

(51) Int. Cl.
*G01N 29/12*    (2006.01)
(52) U.S. Cl.
USPC .......................................... 73/579; 73/54.25
(58) Field of Classification Search
USPC ................................. 73/579, 54.25
See application file for complete search history.

(56) References Cited

U.S. PATENT DOCUMENTS

| | | | |
|---|---|---|---|
| 4,975,577 A | 12/1990 | Franzen et al. | |
| 5,914,553 A | 6/1999 | Adams et al. | |
| 6,757,089 B2 * | 6/2004 | Hayashi | 359/199.1 |
| 7,186,972 B2 | 3/2007 | Farnsworth | |
| 7,451,647 B2 | 11/2008 | Matsuhisa et al. | |
| 7,515,010 B2 * | 4/2009 | Zettl et al. | 331/187 |
| 7,573,625 B2 | 8/2009 | Cannon et al. | |
| 7,724,103 B2 * | 5/2010 | Feng et al. | 331/154 |
| 8,151,368 B2 * | 4/2012 | Kawakatsu et al. | 850/5 |
| 8,427,249 B1 * | 4/2013 | Swanson et al. | 331/154 |
| 2005/0161749 A1 | 7/2005 | Yang et al. | |
| 2008/0295584 A1 | 12/2008 | Cantrell et al. | |

FOREIGN PATENT DOCUMENTS

| | | |
|---|---|---|
| CN | 1632474 A | 6/2005 |
| JP | 9-127005 A | 5/1997 |
| RU | 2 347 191 C1 | 2/2009 |
| WO | WO 2004/041998 A2 | 5/2004 |
| WO | WO 2009/003056 A2 | 12/2008 |

OTHER PUBLICATIONS

M. Park, "Error Analysis and Stochastic Modeling of MEMS based Inertial Sensors for Land Vehicle Navigation Applications," University of Calgary, Dept. of Geomatics Engineering, Apr. 2004, UCGE Reports No. 20194, a Thesis (Abstract).
DeMartini, B.E. et al., "Linear and nonlinear tuning of parametrically eJxcited MEMS oscillators," J. of Microelectromechanical Systems, Apr. 2007, vol. 16, Issue 2, pp. 310-318 (Abstract).
Nayfeh, A.H. et al., "Dynamic pull-in phenomenon in MEMS resonators," Nonlinear Dynamics, Apr. 2007, vol. 48, Nos. 1-2, pp. 153-163 (Abstract).
Gil-Santos, E. et al., "Mass Sensing Based on Deterministic and Stochastic Responses of Elastically Coupled Nanocantilevers," Nano Letters, Amer Chem Society, Sep. 2009, vol. 9 (12), pp. 4122-4127 (Abstract).

* cited by examiner

*Primary Examiner* — J M Saint Surin
(74) *Attorney, Agent, or Firm* — Pauley Petersen & Erickson

(57) ABSTRACT

A system for ultrasensitive mass and/or force detection of this invention includes a mechanical oscillator driven to oscillate in a nonlinear regime. The mechanical oscillator includes a piezoelectric base with at least one cantilever resonator etched into the piezoelectric base. The cantilever resonator is preferably a nonlinear resonator which is driven to oscillate with a frequency and an amplitude. The system of this invention detects an amplitude collapse of the cantilever resonator at a bifurcation frequency as the cantilever resonator stimulated over a frequency range. As mass and/or force is introduced to the cantilever resonator, the bifurcation frequency shifts along a frequency axis in proportion to the added mass.

20 Claims, 5 Drawing Sheets

NONLINEAR NANOMECHANICAL OSCILLATORS FOR ULTRASENSITIVE INERTIAL DETECTION

GOVERNMENT RIGHTS

This invention was made with government support under Contract No. DE-AC05-00OR22725 awarded by the U.S. Department of Energy. The government has certain rights in the invention.

FIELD OF THE INVENTION

The present invention relates to a nanoscale mechanical oscillator for detection of small masses and forces.

BACKGROUND OF THE INVENTION

Nanomechanical and micromechanical oscillators have been explored to enable ultrasensitive mass and/or force detection for use in chemical and biological sensing. Known nanomechanical and micromechanical oscillators have cantilevers, similar to microfabricated cantilevers used in atomic force microscopy (AFM). These cantilevers are driven to oscillate in a linear regime to detect small changes in mass and/or force by measuring changes in a resonance frequency of the cantilevers.

In recent years, a series of nanomechanical oscillators have been developed that are capable of detecting femtogram ($10^{-15}$ g), attogram ($10^{-18}$ g) and zeptogram ($10^{-21}$ g) levels of sensitivity. Theoretically, if all noise except thermal noise is removed from a system, a fundamental limit of an appropriately designed nanomechanical oscillator can approach one atomic mass unit (approximately $1.66 \times 10^{-24}$ g). However, experimentally achievable results of known nanomechanical oscillators are comprised by multiple sources of noise and energy dissipation in addition to thermal noise.

Energy dissipation and thermal noise both tend to randomize a motion of the cantilevers in a manner similar to Brownian motion. As a result, known nanomechanical and micromechanical oscillators are characterized by a relatively wide bell shaped, Lorentizan, resonating curve with uncertainty of a center position in a range of $10^{-3}$ to $10^{-5}$ g. This limits how small of a mass, compared to a mass of the nanomechanical and micromechanical oscillators, can be measured. For example, in order to detect a femtogram ($10^{-15}$ g) level mass change, known nanomechanical and micromechanical oscillators must be smaller than a few micrometers and capable of resonating in a radio frequency range.

In addition to noise, known nanomechanical and micromechanical oscillators are limited by difficulties associated with accurately measuring the resonance frequency of the oscillators. Known nanomechanical and micromechanical oscillators and known methods of detecting mass or force rely on detecting changes in a resonance frequency of the structure, which can be closely approximated by a harmonic, i.e. linear, oscillator. Because the known methods rely on detecting changes in the resonance frequency, they are limited to oscillation amplitudes in the linear regime and thus are limited to a maximum amplitude that is below the nonlinearity onset. This translates into a challenging task of measuring and analyzing oscillation amplitudes as small as $10^{-10}$ m, about the size of a hydrogen atom. Such measurements require the use of sophisticated low-noise optical and electronic components, such as position sensitive detectors, lock-in amplifiers and phased locked loops. These technical challenges of measuring small oscillation amplitudes impede practical applications of such devices.

Other known methods of using nanomechanical and micromechanical oscillators achieve improved stability by exciting large oscillation amplitudes to minimize effects of thermal and ambient noise. However, these known nanomechanical and micromechanical oscillators become nonlinear at large oscillations and the resonance behavior cannot be analyzed using known methods and instruments for linear resonators. In particular, mass loading of nanomechanical and micromechanical oscillators cannot be determined by fitting a resonance curve of the oscillator to a Lorentzian curve or by measuring an output frequency of a self-oscillating circuitry based on a phased-locked loop.

SUMMARY OF THE INVENTION

The present invention is directed to a system for ultrasensitive mass and/or force detection that includes nanoscale and/or microscale mechanical oscillators which are driven to oscillate in a nonlinear regime. By driving the nanoscale and/or microscale mechanical oscillators to oscillate in the nonlinear regime, limitations of previously known resonating nanoscale and microscale structures, such as noise and difficulties with measurements, can be minimized.

According to an embodiment of this invention, the system for ultrasensitive mass and force detection includes a piezoelectric base with at least one cantilever resonator etched into the piezoelectric base. The cantilever resonator is etched into the piezoelectric base such that the cantilever resonator includes a fixed or clamped end attached to the piezoelectric base and a free end extending away from the piezoelectric base. In an alternative embodiment, the cantilever resonator can be formed by any known method including a top-down process such as bulk or surface micromachining or by mounting a separate cantilever resonator to the piezoelectric base.

The cantilever resonator is preferably a nonlinear resonator with nonlinear elasticity that is operated in a mode that includes both a quadratic term and a cubic term. The cubic term arises from stiffening or softening of a material of the cantilever resonator as a degree of deformation increases. However, material properties alone do not give rise to the quadratic term. In an embodiment of this invention, the cantilever resonator includes an asymmetrical geometrical design providing the quadratic term. In a preferred embodiment, the cantilever resonator includes a pre-stressed cantilever with an out-of-plane deformation.

In an embodiment of this invention, the cantilever resonator is driven to oscillate with a frequency and an amplitude by a transducer connected to the piezoelectric base. In an alternative embodiment, the transducer and the piezoelectric base are combined into a single element as a piezoelectric transducer. The transducer is preferably in communication with a digital programmable generator. The digital programmable generator instructs the transducer to excite the cantilever resonator to oscillate over a frequency range. In a preferred embodiment, the cantilever resonator is driven into the nonlinear regime with oscillation amplitudes greater than 5% of a length of the cantilever resonator. In a preferred embodiment, the cantilever resonator can also function as a mechanical demodulator converting the amplitude into a measurable DC signal.

The system of this invention preferably detects a bifurcation point while the cantilever resonator is excited with the digital programmable generator. The bifurcation point is a frequency at which the oscillation amplitude of the cantilever resonator collapses. In an initial state, without an external stimulus such as mass and/or force, the cantilever resonator will reach its bifurcation point at an initial frequency. As mass and/or force is introduced to the cantilever resonator, the bifurcation point of the cantilever resonator shifts along a frequency axis in proportion to added mass and/or force. In operation, the cantilever resonator is driven with the digital programmable generator programmed to sweep a frequency range in a vicinity of the bifurcation point. By using the digital programmable generator, no direct measurement of frequency or any AC signal is required, a time at which the oscillation amplitude collapses defines the bifurcation frequency according to the digital programmable generator.

The system of this invention preferably includes a subsystem to detect the amplitude collapse, the bifurcation point. In an embodiment of this invention, the subsystem to detect amplitude collapse includes a laser positioned over and at an angle to the cantilever resonator such that a laser beam from the laser reflects off the cantilever resonator and projects a laser spot onto a screen. In operation, the cantilever resonator is driven to oscillate at amplitudes of up to several tens of micrometers, sufficient to deflect the laser beam by an angle of tens of degrees. In an embodiment of this invention, the screen is positioned 10 cm from the cantilever resonator which corresponds to approximately a 2 cm span of the laser spot projected onto the screen. The digital programmable generator is programmed to make a continuously repeated linear frequency sweep in a range surrounding and including the bifurcation point. When the frequency reaches the bifurcation point, a sharp drop in the oscillation amplitude is observed and detected with a spot photodetector. By continuously repeating frequency sweeps, the frequency at which bifurcation occurs as a function of time may be monitored with accuracy better than 50 mHz for a structure resonating at approximately 140 kHz. This corresponds to relative accuracy of $3.5 \times 10^{-7}$, an unprecedented value for linear oscillators with similar parameters. Using this approach and an experimental setup that does not require complex electronic components, detection of femtogram level mass changes is possible, a level of performance previously achievable only with much smaller resonators that are very difficult to utilize in a practical device.

BRIEF DESCRIPTION OF THE DRAWINGS

The above-mentioned and other features and objects of this invention will be better understood from the following detailed description taken in conjunction with the drawings wherein.

DETAILED DESCRIPTION OF THE INVENTION

This invention combines unique features of nanoscale/microscale mechanical oscillators with advantages of nonlinear systems. The present invention preferably leverages stochastic resonance, the phenomenon characteristic of certain nonlinear systems in which synergistic action of deterministic and stochastic processes is observed.

Figure 1:
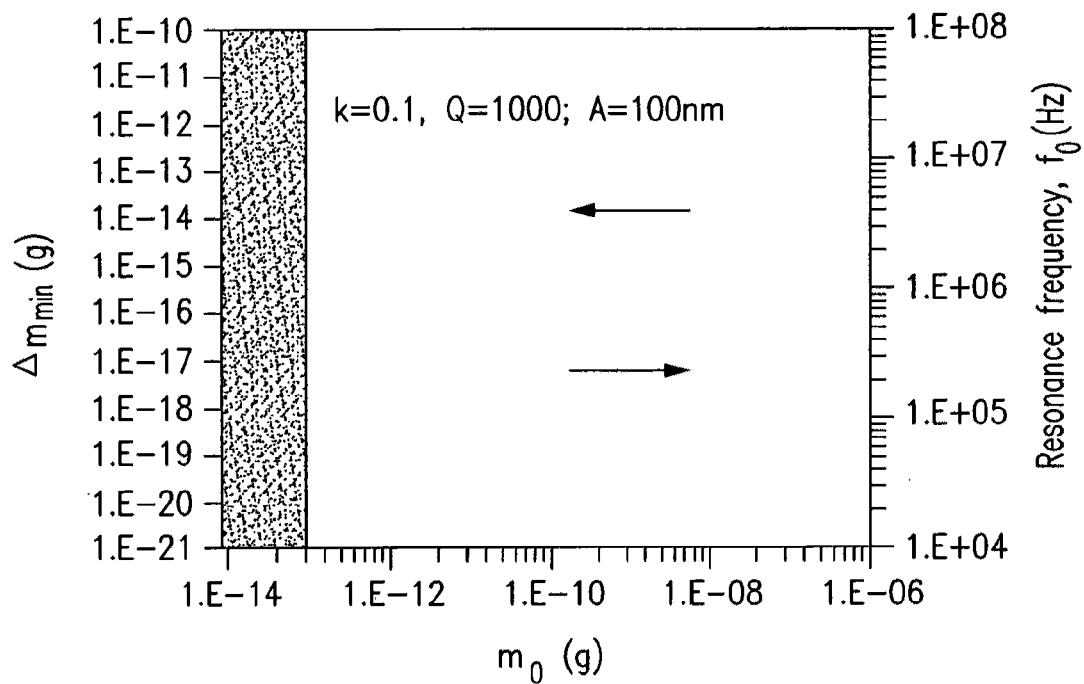
FIG. 1 shows a graphical representation of fundamentally limited mass sensitivity due to thermomechanical noise as a function of a resonator suspended mass.

Generally, in order for a device to have practical utility, linear characteristics of a device is a prerequisite. However, as discussed in the background section, performance of a linear mass sensitive mechanical oscillator is limited by: (i) intrinsic instability of a resonance frequency due to thermal fluctuations; and (ii) accuracy of resonance frequency measurements. The mass sensing performance of a linear mechanical oscillator can be expressed as function of oscillator parameters:

$$\Delta m_{th} = (k_B TB)^{1/2} \frac{8G}{A} \frac{m_0^{5/4}}{k^{3/4} Q^{1/2}} \qquad (1)$$

where $k_B$ is Boltzmann constant, T is a temperature of the device, B is a bandwidth of a measurement, G is a geometric factor (close to unity for a rectangular cantilever), k is a force constant, Q is a mechanical quality factor, $m_0$ is a suspended oscillating mass and A is a rms amplitude of the oscillator motion. Equation 1 may be analyzed by applying a set of constraints that account for technological and methodological limitations. The results of this analysis are shown in FIG. 1.

One conclusion that follows from Equation 1 is that a high mechanical quality factor, Q, i.e. low dissipation, is important. Unfortunately, multiple damping mechanisms of linear mass sensitive resonating devices determine their relatively low Q-factors. Q-factors less than $10^4$ are typical for nanoscale mechanical oscillators operated under ambient conditions while Q-factors close to $10^6$ can only be achieved using larger single-crystal structures in a vacuum.

Optimization of the linear mass sensitive mechanical oscillators, beyond simply scaling down, involves a trade-off between several factors. For example, a thicker and stiffer resonator is less susceptible to thermal noise but is also more difficult to probe because the thicker and stiffer resonator oscillates with a smaller amplitude and at a higher frequency.

The present invention includes a mechanical oscillator that is operated in a nonlinear regime by driving the mechanical oscillator to oscillate with a sufficiently large amplitude. Operation in the nonlinear regime provides a situation where a minute change in mass loading of a driven mechanical oscillator switches the mechanical oscillator into a state of drastically reduced oscillation amplitude, a bifurcation point.

Nonlinear resonance behaviors are described by the following nonlinear differential equation, the Duffing equation:

$$\ddot{x} + \delta \dot{x} + \omega_0^2 x + \beta x^3 = \gamma \cos(\omega t + \phi) \qquad (2)$$

where x is a displacement, $\omega$ is an angular frequency, $\omega_0$ is a resonance frequency, $\phi$ is a phase shift, and $\beta$, $\gamma$ and $\delta$ are parameters related to a cantilever mass, elasticity and losses.

Figure 2:
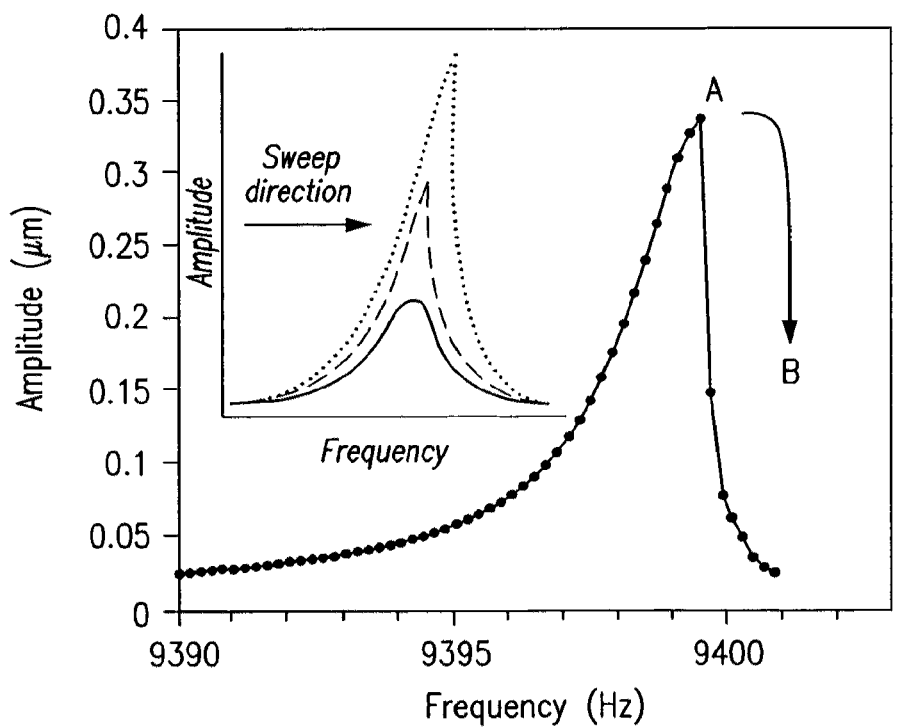
FIG. 2 shows a resonance curve of a nonlinear oscillator with an inset illustrating progressively increased nonlinearity due to increased amplitude.

Solutions of Equation 2 lead to a resonance curve similar to the resonance curve depicted in FIG. 2.

As shown in the inset of FIG. 2, as a relative amplitude of the mechanical oscillator increases, the behavior of the mechanical oscillator deviates significantly from linear. For example, as shown in FIG. 2 moving from point A to point B, a large abrupt change in the oscillator amplitude occurs as a driving frequency exceeds a resonance point of the mechanical oscillator. This point is the bifurcation point. The mechanical oscillator of this invention can be envisioned as a bistable system, in which a transition between the two states can be triggered by extremely small perturbations of a stochastic or deterministic nature. Switching between these states can be detected as a drastic change in the oscillation amplitude.

The system of this invention utilizes the bifurcation point for inertial detection of mass and/or force loading of the mechanical oscillator. In an initial state, without an external stimulus such as mass and/or force, the mechanical oscillator will reach its bifurcation point at an initial frequency. As mass and/or force is introduced to the mechanical oscillator, the bifurcation point of the mechanical oscillator shifts along a frequency axis in proportion to added mass and/or force.

Figure 3:
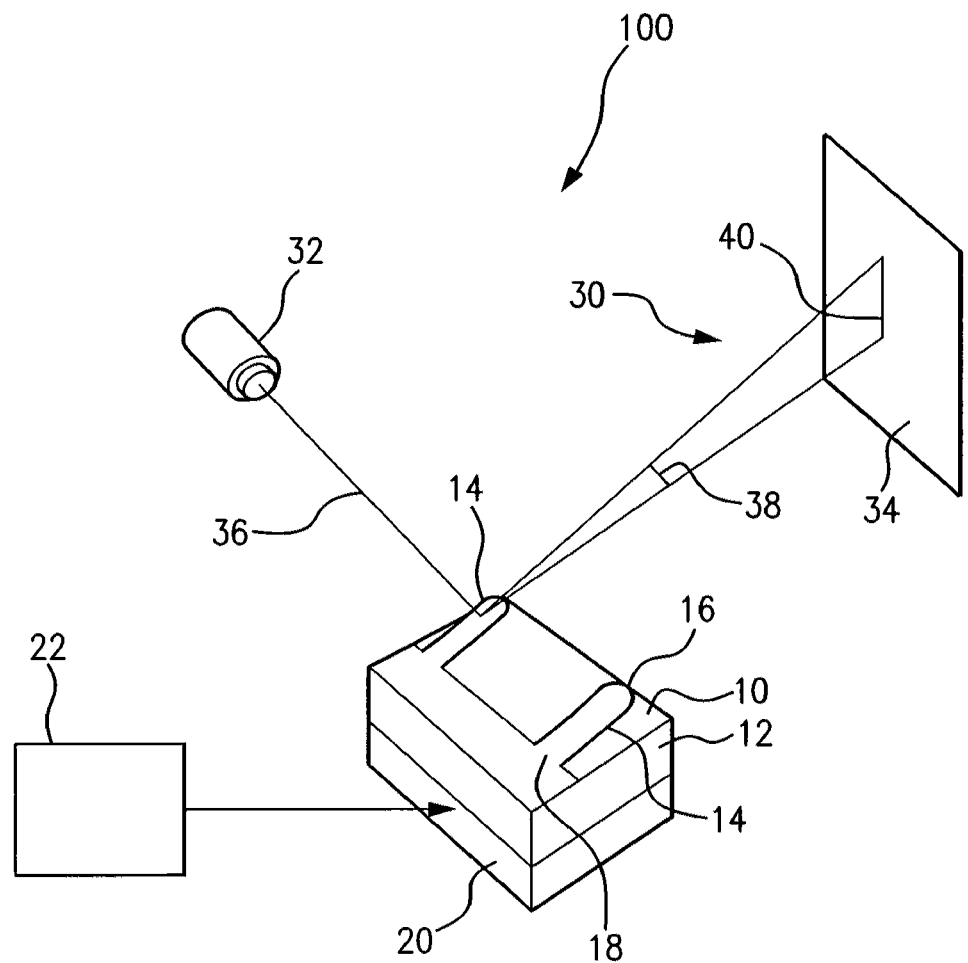
FIG. 3 shows a schematic view of a system of this invention with a microfabricated mechanical oscillator according to an embodiment of this invention.
Figure 4:
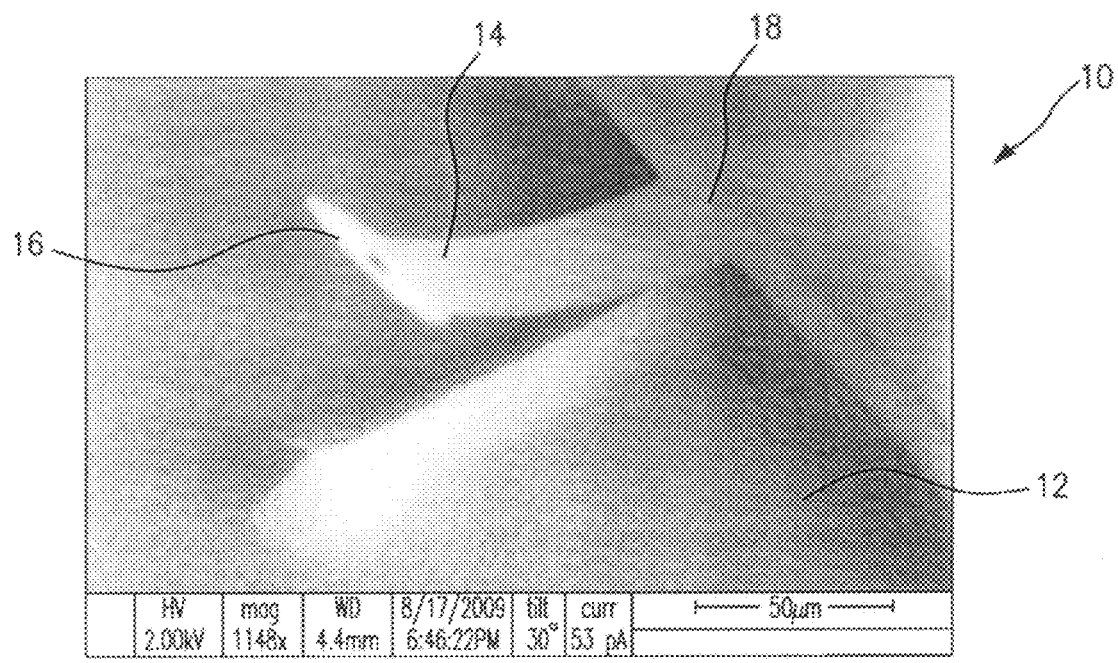
FIG. 4 shows an embodiment of the microfabricated mechanical oscillator including a cantilever resonator exhibiting out of plane deformation due to a nonzero intrinsic stress gradient in a structural material.

FIG. 3 shows an embodiment of a system 100 of this invention including a microfabricated mechanical oscillator 10. FIG. 4 shows a photograph of a magnified view of the microfabricated mechanical oscillator 10 according to an embodiment of this invention. In this embodiment, the microfabricated mechanical oscillator 10 includes a piezoelectric base 12 with a cantilever resonator 14 connected to the piezoelectric base 12. The piezoelectric base 12 is preferably manufactured from a semiconductor material such as, but not limited to, silicon. In an alternative embodiment, the substrate can be manufactured from a variety of materials including, but not limited to, silicon nitride, silicon oxide, aluminum oxide and aluminum nitride.

In an embodiment of this invention, the cantilever resonator 14 includes a free end 16 and a fixed end 18, the fixed end 18 mounted to the piezoelectric base 12 and the free end 16 extending away from the piezoelectric base 12. The cantilever resonator 14 is preferably manufactured from a semiconductor material such as, but not limited to, silicon. In an alternative embodiment, the substrate can be manufactured from a variety of materials including, but not limited to, silicon nitride, silicon oxide, aluminum oxide and aluminum nitride. In a preferred embodiment, the cantilever resonator 14 is manufactured with a length ranging from 1 to $10^3$ micrometers, a width ranging from 0.10 micrometers, and a thickness ranging from 5 to 5000 nanometers. The cantilever resonator is also capable of oscillating with an amplitude greater than 5% of the length and preferably greater than 10% of the length. In a preferred embodiment, the cantilever resonator is capable of oscillating with an amplitude greater than 10 micrometers. In the embodiment shown in FIG. 4, the cantilever resonator 12 includes a fixed end 18 with a single-clamped structure, however, the cantilever resonator 12 can include any number of clamping points including a double-clamped structure.

In a preferred embodiment, the microfabricated mechanical oscillator 10 includes a plurality of cantilever resonators 14 formed in an array. The array may be a linear, tessellated, symmetric or any other preferable array.

Figure 5:
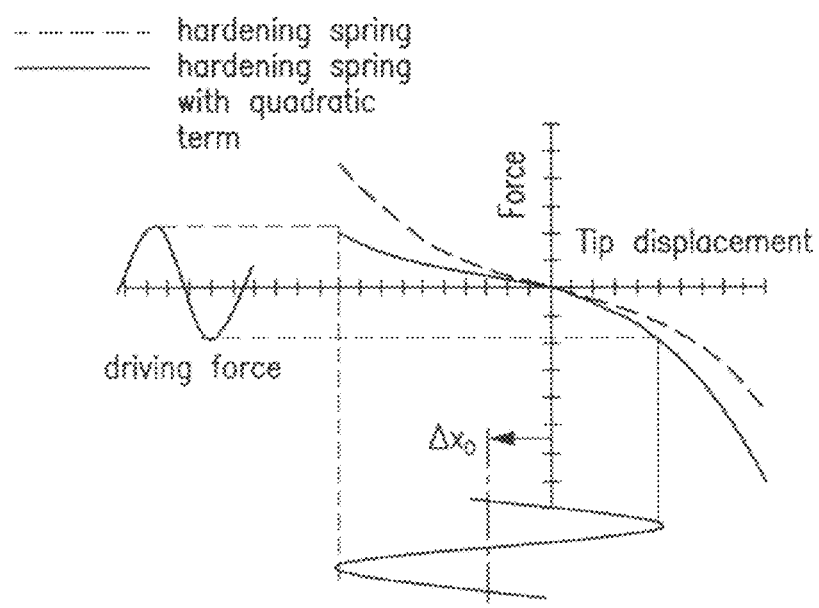
FIG. 5 shows a graphical representation of mechanical signal demodulation using a cantilever resonator with a quadratic term in nonlinear elasticity.
Figure 6:
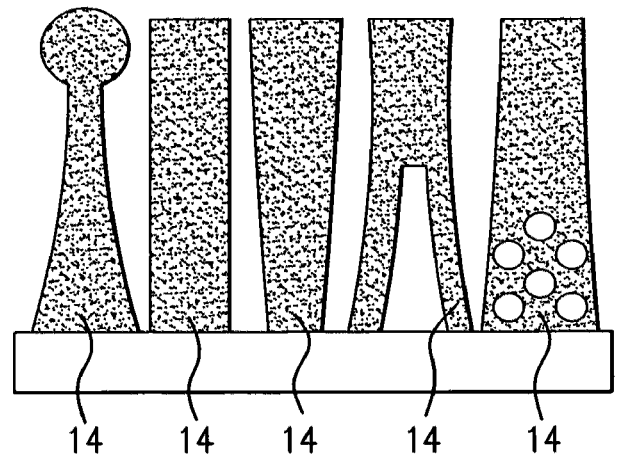
FIG. 6 shows schematic top views of various shapes of the cantilever resonator.

The microfabricated mechanical oscillator 10 of this invention takes advantage of a nonlinear elasticity of the cantilever resonator 14 which includes a quadratic nonlinear term in addition to other possible nonlinear terms. A force response of such a nonlinear element, can be expressed as:

$$F = -kx - bx^2 - ax^3 \quad (1)$$

where k, b, and a are respectively, a linear term, a quadratic term and a cubic term describing the cantilever resonator 14 elasticity, x is a displacement characterizing the cantilever resonator's deformation relative to a equilibrium state. The cubic term in Equation 1 is related to the fact that all known materials undergo either stiffening or softening as the degree of their deformation increases. However, material properties alone do not give rise to the quadratic term in Equation 1. In the embodiment of FIG. 4, the cantilever resonator 14 includes an asymmetric geometrical design in order to have control over the quadratic term in Equation 1. In the embodiment of FIG. 4, the cantilever resonator 14 is a pre-stressed cantilever with a substantial out-of-plane deformation. In this embodiment, an asymmetric force versus displacement characteristics can be achieved. As a result of the quadratic term, a center of oscillator mass averaged over a period of oscillation depends on the oscillation amplitude. Therefore, as shown in FIG. 5, slow changes, $\Delta x_o = f(t)$, in the center of oscillator mass provides amplitude demodulation for high frequency cantilever resonator 14 oscillations. Alternative embodiments of the cantilever resonator 14 can have any shape including, but not limited to, the shapes shown in FIG. 6.

Figure 7:
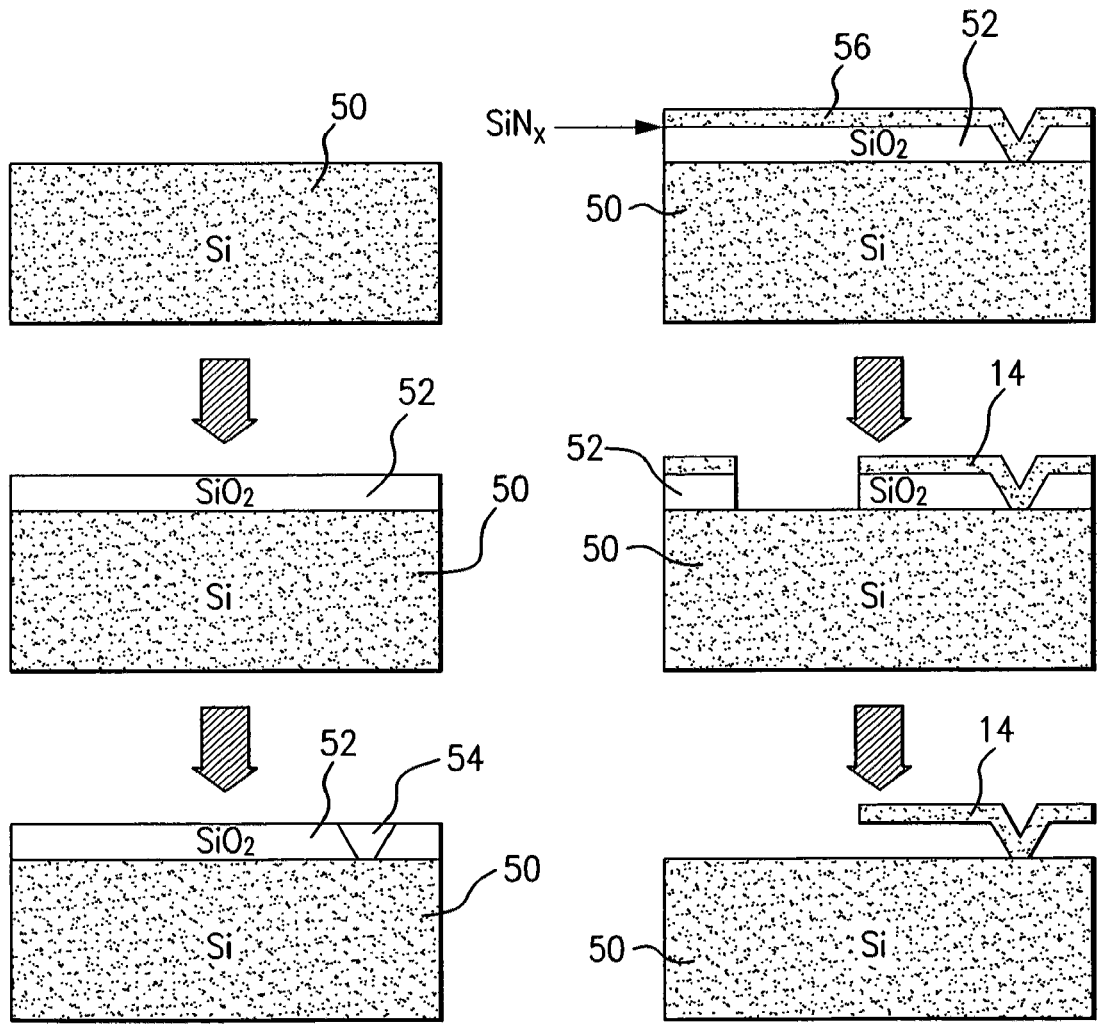
FIG. 7 shows schematic side views of preferred steps involved in fabrication of the microfabricated mechanical oscillator.

FIG. 7 shows an embodiment of a preferred method for manufacturing the piezoelectric base 12 and the cantilever resonator 14 of this invention. This method uses photolithography fabrication steps to construct the piezoelectric base 12 and the cantilever resonator 14. The process begins with a silicon (Si) wafer 50. A sacrificial layer of silicon dioxide 52 ($SiO_2$) is then applied to the Si wafer 50 using plasma-enhanced chemical vapor deposition (PECVD). Next an anchoring point 54 for the fixed end 18 is etched into the sacrificial layer of $SiO_2$ 52 using reactive ion etching (RIE). A layer of low stress silicon nitride 56 ($SiN_x$) is then applied to the sacrificial layer of $SiO_2$ 52 and the anchoring point 54 using PECVD as a structural layer. Next, the cantilever resonator 14 is patterned using RIE etching. In the next step the sacrificial layer of $SiO_2$ 52 is removed with a wet etch. In an alternative embodiment, the above process can be adapted to use single crystal Si, amorphous Si or low stress silicon nitride ($SiN_x$) as a structural layer. These materials are known for their excellent chemical stability, mechanical properties and compatibility with a variety of patterning/etching techniques.

As shown in FIG. 3, an embodiment the system 100 of this invention further includes a transducer 20 in connection with the piezoelectric base 12 to drive the cantilever resonator 14 to oscillate at an amplitude and a frequency. According to this invention, the transducer 20 is capable of driving the cantilever oscillator 14 with the amplitude greater than 5% of the length of the cantilever oscillator and preferably with the amplitude greater than 10% of the length of the cantilever oscillator. The transducer 20 is preferably also capable of driving the cantilever oscillator at a frequency ranging from 10 kHz to 100 MHz. In an alternative embodiment of this invention, the transducer 20 can be combined with the piezoelectric base 12 to form a piezoelectric transducer.

In FIG. 3, a sweep generator 22 is in communication with the transducer 20 to excite the transducer 20 to drive the cantilever resonator 14 at the frequency. In a preferred embodiment, the sweep generator 22 is a digital programmable sweep generator that is capable of exciting the transducer 20 over a frequency range.

The system 100 of this invention further includes a subsystem 30 to detect amplitude collapse, the bifurcation point, of the cantilever resonator 14. In the embodiment shown in FIG. 3, the subsystem 30 includes a laser 32 positioned over and at an angle to the microfabricated mechanical oscillator 10 and a screen 34 positioned on an opposite side of the microfabricated mechanical oscillator 10 as the laser 32. In operation, the laser 32 shines a laser beam 36 on the cantilever resonator 14 and is reflected onto the screen 34. The oscillations of the cantilever 14 are sufficient to deflect the laser beam 36 through an angle 38 which is shown as a span 40 on the screen 34. In a preferred embodiment, the angle 38 of deflection is greater than ten degrees. When the cantilever resonator 14 reaches the bifurcation point, a sharp drop in the oscillation amplitude can be visualized as a reduction in a length of the span 40. In a preferred embodiment, the system 100 may further include at least one of a spot photodetector and a position sensitive photodetector to detect the amplitude collapse. In an embodiment, the spot photodetector can comprise a single element photodiode.

For example, in one embodiment of this invention, the cantilever resonator measures approximately 50 by 120 micrometers and oscillates with the amplitude measuring several tens of micrometers. As the cantilever resonator oscillates it will deflect the laser beam over an angle measuring approximately 10 degrees. This corresponds to a 2 cm span of the laser spot projected on the screen positioned 10 cm from the cantilever oscillator.

In operation, the sweep generator 22 instructs the transducer 20 stimulate the cantilever resonator 14 to oscillate over a frequency range in a vicinity of and including the device resonance. At each frequency the cantilever resonator will oscillate at an amplitude. At the bifurcation point the amplitude will collapse. A sequence of abrupt signal changes due to the amplitude collapse upon repeated frequency sweeping is used to trigger a frequency readout, thus producing a data series in which frequency is function time. When a digitally programmable sweep generator is used, no direct measurements of frequency or any AC signals are necessary. The time at which output signal of the spot photodetector abruptly changes unambiguously defines a frequency value of the bifurcation point.

Figure 8:
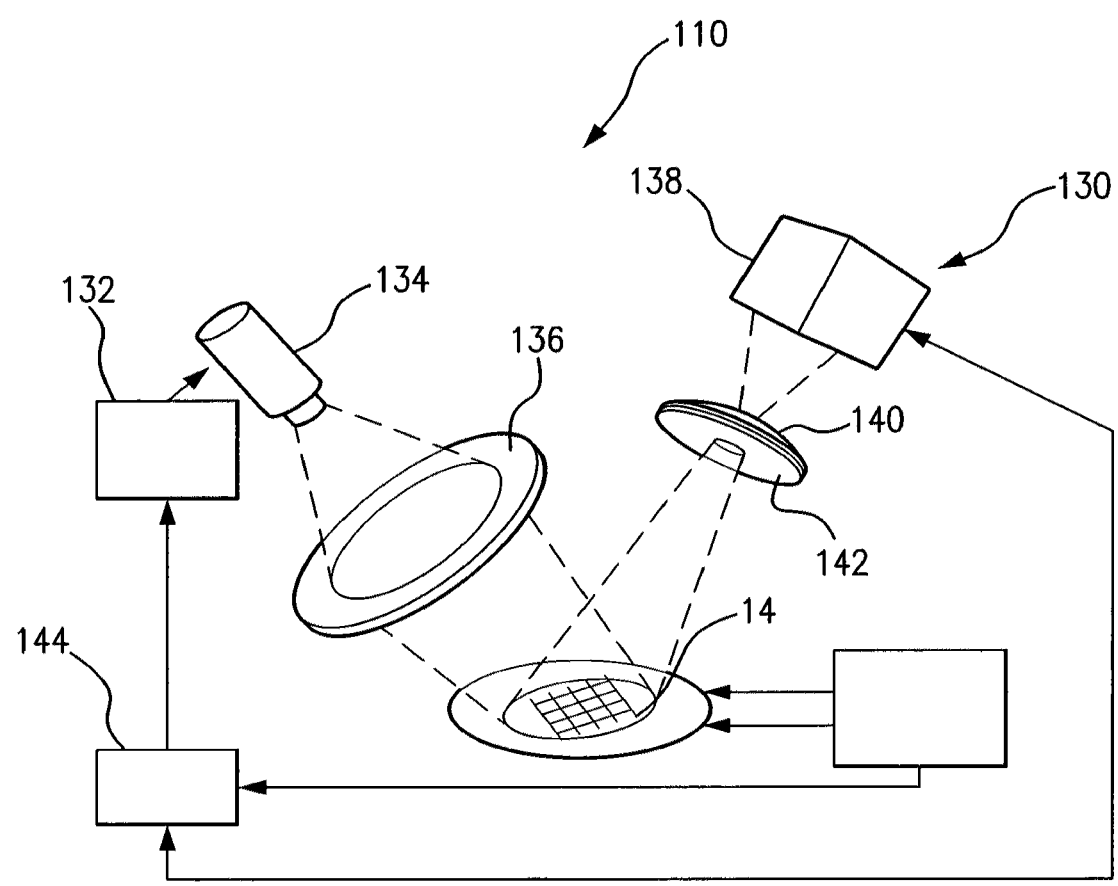
FIG. 8 shows a schematic view of an alternative system of this invention with the microfabricated mechanical oscillator according to an embodiment of this invention.

FIG. 8 shows another embodiment of the system 110 of this invention with an alternative subsystem 130 for detecting the amplitude collapse of the cantilever resonator 14. This subsystem 130 is an optical readout system. The optical readout system includes a driver 132 and a light source 134 positioned over and at an angle to the cantilever resonator 14. In a preferred embodiment, the light source 134 is a modulated light source. Light from the light source 134 passes through projecting optics 136 and onto the microfabricated mechanical oscillator 10. The light then reflects off the cantilever resonator 14 and into a digital camera 138. In a preferred embodiment, the reflected light passes through at least one of imaging optics 140 and a spatial filter 142 before being recorded by the digital camera 138, preferably a charge coupled device (CCD) or a CMOS sensor. A recorded motion of the oscillations of the cantilever resonator 14 is received and processed by a digital signal processor 144 to detect a collapse of the oscillation amplitude of the cantilever resonator 14. In an embodiment of this invention, the alternative subsystem 130 further includes a stroboscopic video analyzer, a frequency modulated phase-locked loop (FM-PLL), and a high magnification, diffraction limited, optics.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A method for ultrasensitive mass and force detection comprising:
    mounting a cantilever resonator on a piezoelectric transducer;
    driving the piezoelectric transducer to oscillate the cantilever resonator with an amplitude over a frequency range;
    deflecting a laser beam focused at an angle on the cantilever resonator;
    projecting the deflected laser beam as a spot with an oscillation amplitude onto a screen; and
    detecting a bifurcation frequency of the cantilever resonator as a drop in the oscillation amplitude.

2. The method of claim 1 further comprising:
    detecting the bifurcation frequency with a spot photodetector.

3. The method of claim 1, wherein the angle in the deflecting step is greater than ten degrees.

4. The method of claim 1, wherein the cantilever resonator is driven to oscillate in a nonlinear range.

5. The method of claim 4, wherein the amplitude of the cantilever resonator is greater than ten micrometers.

6. The method of claim 1, wherein a digital programmable sweep generator drives the piezoelectric transducer to oscillate the cantilever resonator over the frequency range.

7. The method of claim 1, wherein the mounting step further comprises:
    mounting an array of cantilever resonators etched on a chip on the piezoelectric transducer.

8. A system for ultrasensitive mass and force detection comprising:
    a piezoelectric base;
    a cantilever resonator including a free end and a fixed end, the fixed end attached to the piezoelectric base and the free end extending away from the piezoelectric base;
    a transducer connected to the piezoelectric base to drive the cantilever resonator to oscillate at an amplitude and a frequency;
    a digital programmable sweep generator in communication with the transducer to excite the cantilever resonator over a frequency range;
    a laser including a laser beam focused at an angle to the cantilever resonator;
    wherein the digital programmable generator sweeps the transducer across the frequency range to determine a bifurcation frequency and the system detects an external stimuli by measuring shifts of the bifurcation frequency.

9. The system of claim 8 wherein the transducer drives the cantilever resonator into a nonlinear resonance.

10. The system of claim 8, wherein the cantilever resonator is a nonlinear resonator with a nonlinear elasticity.

11. The system of claim 8, wherein the piezoelectric base and the transducer are combined as a piezoelectric transducer.

12. The system of claim 8 further comprising:
    an array of cantilever resonators attached to the piezoelectric base.

13. The system of claim 8, wherein the cantilever resonator is etched into the piezoelectric base.

14. The system of claim 8, wherein the cantilever resonator oscillates at an amplitude of greater than 5% of a length of the cantilever resonator.

15. The system of claim 8, wherein the cantilever resonator includes an asymmetric geometrical design.

16. The system of claim 15, wherein the cantilever resonator includes an out-of-plane deformation.

17. The system of claim 8, wherein the cantilever resonator functions as a mechanical demodulator converting the amplitude into a measurable DC signal.

18. A system for ultrasensitive mass and force detection comprising:
- a piezoelectric base;
- a transducer connected to the piezoelectric base;
- a cantilever resonator including a free end and a fixed end, the fixed end mounted to the piezoelectric base and the free end extending away from the piezoelectric base;
- a driver in electrical communication with a modulated light source and a projecting optics, the modulated light source and the projecting optics directing light on the cantilever and the piezoelectric base;
- a digital camera, an imaging optics and a spatial filter positioned over the piezoelectric base and the beam to capture a reflected light from the piezoelectric base and the cantilever; and
- wherein the transducer drives the cantilever into a nonlinear resonance and the system detects an external stimuli by measuring shifts in a bifurcation point.

19. The system of claim 18, wherein the cantilever resonator is a nonlinear resonator with a nonlinear elasticity.

20. The system of claim 18, wherein the cantilever resonator includes an asymmetric geometrical design and an out-of-plane deformation.

* * * * *